(12) United States Patent
Von Roden

(10) Patent No.: US 8,731,643 B2
(45) Date of Patent: May 20, 2014

(54) IMAGING SYSTEM AND METHODS FOR MEDICAL NEEDLE PROCEDURES

(75) Inventor: Martin Von Roden, Möhrendorf (DE)

(73) Assignee: Siemens Aktiengesellschaft, München (DE)

( * ) Notice: Subject to any disclaimer, the term of this patent is extended or adjusted under 35 U.S.C. 154(b) by 1326 days.

(21) Appl. No.: 11/939,252

(22) Filed: Nov. 13, 2007

(65) Prior Publication Data

US 2009/0124895 A1 May 14, 2009

(51) Int. Cl.
*A61B 5/05* (2006.01)

(52) U.S. Cl.
USPC .............................. 600/427; 600/407; 600/424

(58) Field of Classification Search
USPC ......... 600/407, 410, 414, 424, 425, 426, 427, 600/429, 437, 443; 606/130
See application file for complete search history.

(56) References Cited

U.S. PATENT DOCUMENTS

| 2007/0055131 A1 | 3/2007 | Deinzer et al. | |
| 2007/0167762 A1* | 7/2007 | Kim et al. | 600/437 |
| 2008/0097165 A1* | 4/2008 | Gattani et al. | 600/300 |
| 2008/0167545 A1* | 7/2008 | Meissner et al. | 600/407 |
| 2008/0167551 A1* | 7/2008 | Burns et al. | 600/427 |

\* cited by examiner

*Primary Examiner* — Unsu Jung
*Assistant Examiner* — Christopher Cook
(74) *Attorney, Agent, or Firm* — Lempia Summerfield Katz LLC

(57) ABSTRACT

A method for planning a needle path is provided. The method includes displaying a restricted region on a display, the restricted region being defined by spatial limitations of an imaging system and a location of a selected target point; and selecting a skin entry point outside the restricted region.

21 Claims, 3 Drawing Sheets

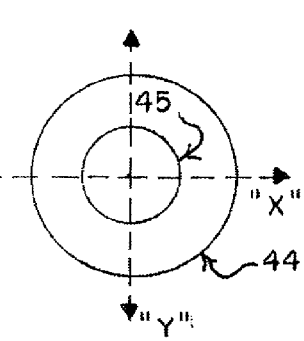
FIG.1A
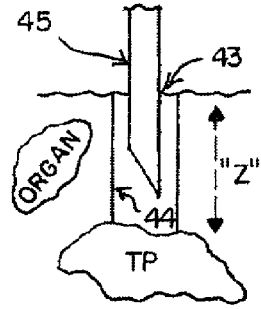
FIG.1B
FIG.1C
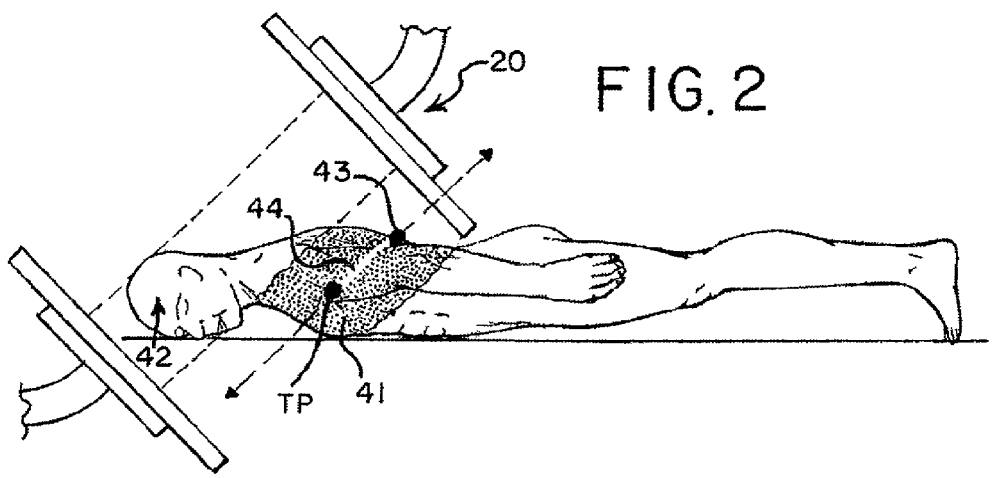
FIG.2
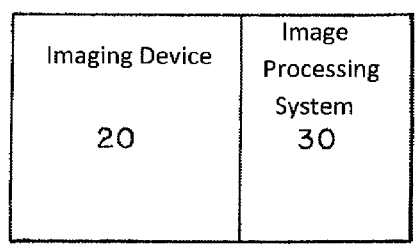
FIG.3

IMAGING SYSTEM AND METHODS FOR MEDICAL NEEDLE PROCEDURES

BACKGROUND

A needle may be used during a medical procedure, which may include biopsies, RF ablations, vertebroplasties, kyphoplasties, or other treatment or diagnosis procedures. Medical needle procedures include two stages. The first stage includes planning the needle path. The second stage includes monitoring the progress of the needle. To monitor the progress of the needle during the medical procedure, an imaging system is used to view the needle relative to the planned needle path.

An imaging system obtains a top-view image (FIG. 1B) and a side-view image (FIG. 1C) of the needle path. To obtain the top-view image, the imaging device is disposed along the needle path axis (e.g., the z-axis in FIG. 1A). To obtain the side-view image, the imaging device is disposed orthogonal (e.g., in the x-y plane in FIG. 1A) to the needle path axis.

After planning the needle path, the physician is required to check whether the imaging system is capable of being disposed in the required positions. Depending on the selected needle path, the imaging system may be unable to be disposed in the required positions because of structural limitations of the imaging system. If the imaging system is unable to be disposed in the required positions, the physician must re-plan the needle path. The physician continues to plan and check until the imaging system is able to physically obtain the necessary images.

Therefore, there is a need for an imaging system that displays a restricted region, which is defined by structural limitations of the imaging device and the location of the target point, such that the physician may choose a needle path that may examined by an imaging device disposed in the required positions during the needle progression.

SUMMARY

The present embodiments relate to planning a needle path by displaying a restricted region on a display. The restricted region is defined by structural limitations of an imaging device relative to a selected target point. The displayed restricted region allows a physician to choose a needle path that is disposed in a region outside the restricted region.

In one embodiment, an imaging system includes a display; a processor; and an imaging device. The processor is operable to determine a restricted region being defined by one or more spatial limitations of the imaging device and a location of a target point of the needle path.

In one embodiment, a method for planning a needle path is provided. The method includes displaying a restricted region on a display, the restricted region being defined by spatial limitations of an imaging system and a location of a selected target point; and selecting a needle path outside the restricted region.

In one embodiment a method for planning needle progression views for during therapy; the method comprising: displaying a restricted region on a display, the restricted region being defined by spatial limitations of an imaging system and a location of a needle path; and selecting a first progression view that is in-line with the needle path, the first progression view being disposed outside the restricted region.

In one embodiment, a computer readable storage media stores data representing instructions executable for planning a needle path. The instructions include displaying a restricted region on a display, the restricted region being defined by spatial limitations of an imaging system and a location of the selected target point.

BRIEF DESCRIPTION OF THE FIGURES

FIGS. 1A, 1B, and 1C illustrate one embodiment of a needle path and associated views.

FIG. 2 illustrates a needle path outside a possible imaging area.

FIG. 3 illustrates one embodiment of an imaging system.

DETAILED DESCRIPTION

Figure 4:
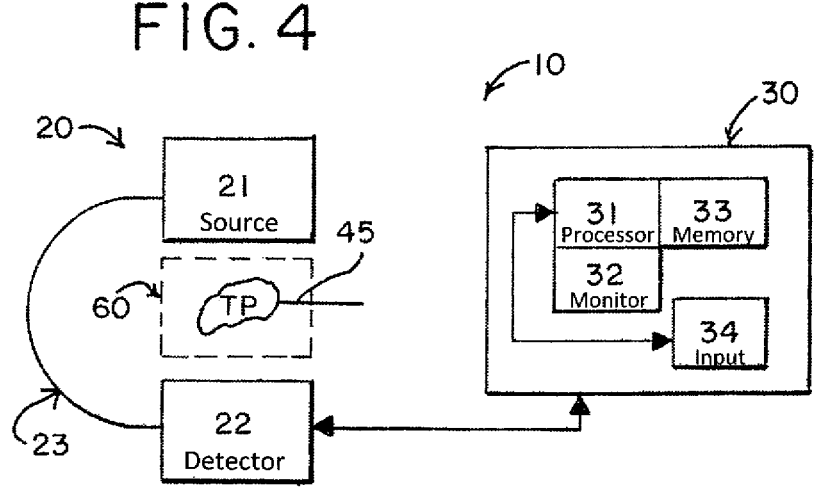
FIG. 4 illustrates one embodiment of an imaging device and an image processing system.

The present embodiments provide a software based planning tool that visually indicates in a three-dimensional (3D) dataset the needle path planning. The planning tool considers the geometrical constraints of the connected C-arm system. The planning tool takes the geometrical constraints into account and provides possible cones where a needle path can be positioned. During the planning procedure, visual feedback is used to indicate if the currently planned needle path may be imaged with the acquisition system. In one embodiment, the software inhibits (prevents) the user from selecting a skin entry point, during the planning phase, which would not be reachable by possible C-arm angulations. This can accelerate the planning workflow because it avoids trial and error steps until a needle path is found that is also reachable by the C-arm.

FIG. 3 shows one embodiment of an imaging system 10 for needle work. The imaging system 10 may include an imaging device 20 and an image processing system 30. Additional, different, or fewer components may be provided.

The imaging system 10 is a medical workstation, a computed tomography (CT) system, a magnetic resonance system, an angiography system, fluoroscopy system, or other now known or latter developed imaging systems. For example, the system 10 may be a C-arm based X-ray system. The imaging system 10 may be used to plan a needle path, avoid or correct needle misdirection during a procedure, or generate images of a patient's body. For example, the imaging system 10 is a workstation for planning a needle path. The workstation receives one or more images of a dataset of a region to be examined. The workstation provides assistance to a physician for planning the needle path. The needle path may be fully or partially planned by the workstation. In another example, the imaging system 10 provides a visualization of a treatment device, such as a needle 45, in relation to a region 60 to be examined, recorded, or imaged.

FIG. 4 illustrates one embodiment of an imaging device 20. The imaging device 20 may include an imaging source 21 and an imaging detector 22. Additional, different, or fewer components may be provided. The imaging device 20 may be a C-arm computed tomography device, gantry computed tomography device, a magnetic resonance device, an angiography device, a fluoroscopy device, C-arm based X-ray system or other now known or later developed imaging devices.

The imaging source 21 and imaging detector 22 may be disposed opposite each other. For example, the imaging source 21 and imaging detector 22 may be disposed on diametrically opposite ends of a C-arm 23. In another example, the source 21 and detector 22 are connected inside a gantry. The region 60 to be examined is located between the source 21 and detector 22. The size of the region 60 to be examined may be defined by the amount, shape, or angle of radiation. The region 60 to be examined may include the target point (TP), the needle 45, all or a portion of a patient, and a surrounding area. For example, a physician may desire to provide treatment, using a needle 45, to a tumor located on a patient's spinal cord. The tumor is the target point (TP). The region 60 to be examined includes the tumor, a portion of the spinal cord, lungs, heart, or other organs or body parts in the surrounding area of the tumor.

The imaging source 21 may be a radiation source, such as an x-ray source. The imaging source 21 may emit radiation to the detector 22. The imaging detector 22 may be a radiation detector, such as a digital or film based x-ray detector. The imaging detector 22 may detect the radiation emitted from the imaging source 21. Image data is generated based on the amount or strength of radiation detected. For example, the imaging detector 22 detects the strength of the radiation received at the imaging detector 22 and generates image data based on the strength of the radiation. In an alternate embodiment, the imaging source 21 is a magnetic resonance source.

The image data may be two-dimensional (2D) data or three-dimensional (3D) data. For example, a computer tomography (CT) device may obtain 2D image data or 3D data. In another example, a fluoroscopy device may obtain 3D representation data. In another example, an ultrasound device may obtain 3D representation data by scanning the region 60 to be examined. The image data may be obtained from different directions. For example, the imaging device 20 may obtain sagittal, coronal, or axial image data. In another example, the imaging device 20 obtains image data from a needle path axis direction, which is the z-direction in FIG. 1A.

The imaging device 20 may be communicatively coupled to the image processing system 30. The imaging device 20 may be connected to the image processing system 30 by a communication line, cable, wireless device, communication circuit, or other communication device. For example, the imaging device 20 may communicate the image data to the image processing system 30. In another example, the image processing system 30 may communicate an instruction, such as a position or angulation instruction, to the imaging device 20. All or a portion of the image processing system 30 may be disposed in the imaging device 30, in the same or different rooms as the imaging device 30, or in the same or different facilities.

FIG. 4 also illustrates one embodiment of an image processing system 30. The image processing system 30 may include a processor 31, monitor 32, and a memory 33. Additional, different, or fewer components may be provided. For example, the image processing system 30 may include an input device 34.

The processor 31 is a general processor, digital signal processor, application specific integrated circuit, field programmable gate array, analog circuit, digital circuit, combinations thereof, or other now known or later developed processor. The processor 31 may be a single device or a combination of devices, such as associated with a network or distributed processing. Any of various processing strategies may be used, such as multi-processing, multi-tasking, parallel processing, or the like. The processor 31 is responsive to instructions stored as part of software, hardware, integrated circuits, firmware, micro-code or the like.

The processor 31 may generate an image from the image data. The processor 31 processes the image data from the imaging device 20 and generates an image based on the image data. For example, the processor 31 may generate one or more fluoroscopic images, top-view images, in-plane images, orthogonal images, side-view images, 2D images, 3D representations, progression images, multi-planar reconstruction images or other images from the image data. In another example, a plurality of images may be generated from image data detected from a plurality of different positions or angles of the imaging device 20.

A plurality of generated images or image data may be associated with a characteristic, such as a patient's name, body part, or other characteristic that relates to the plurality of images. The associated images may be a set of images. For example, a set of images may relate to a patient. In another example, the set of images may have a sub-classification of images, such as spinal-cord images, head images, or leg images.

The processor 31 may generate a 2D image from the image data. The 2D image may be planar slice of the region 60 to be examined. For example, a C-arm computer tomography device may be used to detect image data that may be used to generate a sagittal image (image A), a coronal image (image B), and an axial image (image C). The sagittal image is a side-view image of the region 60 to be examined. The coronal image is a front-view image of the region 60 to be examined. The axial image is a top-view image of the region 60 to be examined. In FIG. 5, images A, B, C, and D illustrate a patient's spinal cord region.

Figure 5A:
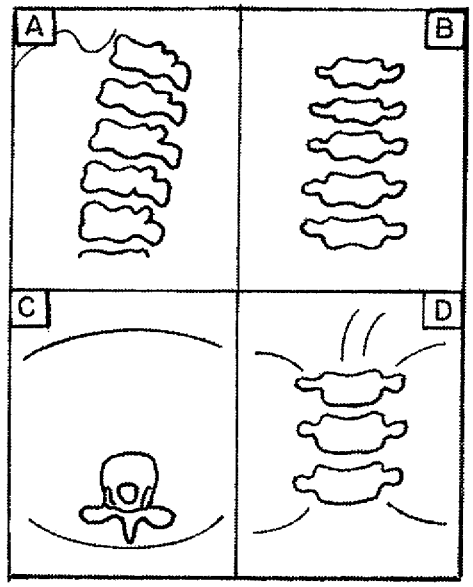
FIGS. 5A-5D illustrate one embodiment of a display with images of a region to be examined displayed thereon.

The processor 31 may generate a 3D representation from the image data. The 3D representation illustrates the region 60 to be examined. The 3D representation may be generated by combining 2D images obtained by the imaging device 20 from a given viewing direction. For example, as shown in FIG. 5A, a 3D representation (image D) may be generated by analyzing and combining a sagittal image (image A), a coronal image (image B), and an axial image (image C). Additional, different, or fewer images may be used to generate the 3D representation. Generating the 3D representation is not limited to combining 2D images, for example, any now known or later developed method may be used to generate the 3D representation.

The processor 31 may display the generated images on the display 33. For example, as shown in FIG. 5A, the processor 31 may generate images A, B, C, and D and communicate the images A, B, C, and D to the display 33. The images A, B, C, and D may be displayed on the display 33. As discussed above, the processor 31 may generate a set of images having one or more images. All or a portion of these images may be displayed on the display 33. A user may navigate, scroll, or browse a set of images, for example, using the input device 34. For example, a patient-specific set of images may include twenty (20) different images, each image illustrating all or a portion of the region 60 to be examined, from different angles, different viewing points, and/or different depths. As shown in FIG. 5, the display 33 displays four (4) of the images at a time. A user may view all twenty (20) of the images by scrolling, navigating, or browsing the entire set of images. Other numbers of images may be displayed.

The processor 31 may communicate with the memory 32. The processor 31 and memory 32 may be connected by a cable, circuit, wireless-connection, or other communication coupling. Images, data, and other information may be communicated from the processor 31 to the memory 32 or viceversa. For example, the processor 31 may communicate the generated images, image data, or other information to the memory 32. The processor 31 may retrieve information, images, image data, or other data from the memory 32. For example, the processor 31 may retrieve a target point (TP) location stored in the memory 32. In another example, the processor 31 may retrieve patient data from the memory 32. The patient data may be used by the processor 31 to communicate instructions or requests to the imaging device 20. The patient data may include a patient's medical condition, size, positioning requirements, structural limitations, or other patient information. In another example, the processor 31 may retrieve structural limitation data stored in the memory 32.

The processor 31 may mark a selected target point (TP). For example, a target point (TP) may be selected in a first image, such as image A of FIG. 5A. The selected target point (TP) may be selected by the processor 31 or by a user, for example, using an input device 34. The processor 31 may generate a marking, such as the dot in image A of FIG. 5B, and display the marking on the image shown on the display 33. For example, the marking may be superimposed on displayed or non-displayed images. The processor 31 or user may analyze the location of the selected target point (TP) and determine a target point (TP) location for other displayed or non-displayed images (e.g., images B, C, and D). The processor 31 displays a marking at the location on the other displayed or non-displayed images.

The target point markings illustrate the location of the selected target point (TP) on each of the displayed images. For example, a tumor may be located on the L-2 vertebrae of the spinal cord. A physician may view the images of FIG. 5B (e.g., by browsing through a set of images) and select a target point (TP) located on the L-2 vertebrae, as shown in image A, using the input device 34. The processor 31 superimposes a marking at the target point (TP) location in image A. The processor 31 may also superimpose a marking at the corresponding target point (TP) locations in images B-D.

Figure 5B:
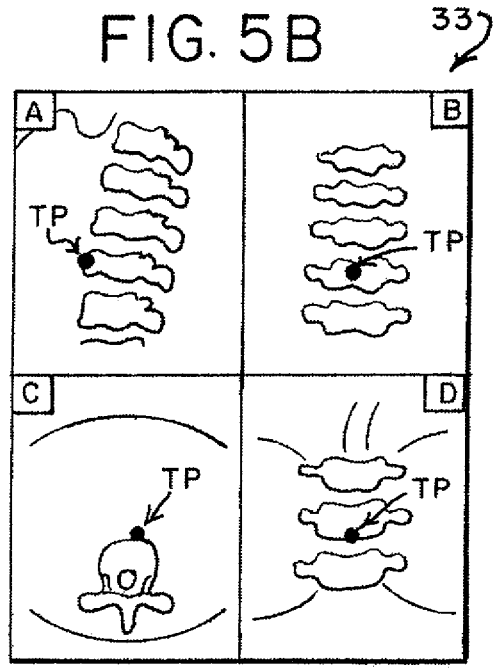
Figure 5C:
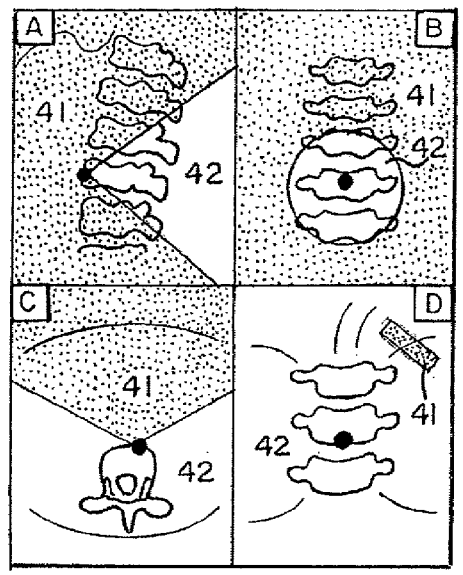

As shown in FIG. 5C, the processor 31 may define a restricted region 41. The restricted region 41 is defined by structural limitations of the imaging device 20 and the location of the target point (TP). The imaging device 20 is physically unable to be positioned or angled to monitor a needle 45 progression relative to a needle path 44, if the needle path 44 is located in the restricted region 41. For example, the imaging device 20 is unable to obtain certain images, such as top-view image or side-view image, if the needle path 44 is positioned in the restricted region 41.

A structural limitation may include a size limitation, rotational limitation, patient limitation or other geometric limitations of the imaging system. For example, size limitations may include the size of the imaging device, the size of the patient, and the size of the patient support. In another example, rotational limitations may include the ability of the imaging device to rotate to certain positions, the ability of the patient to rotate into certain positions, and the ability of the patient support to rotate into certain positions. In anther example, a structural limitation may include any limitation that prevents the imaging device 20 from being positioned into a position relative to the patient.

FIG. 2 illustrates an imaging device 20 and a corresponding restricted region 41. One structural limitation of the imaging device 20 is the size of the imaging device 20. For example, the imaging device 20, such as a C-arm CT device, may not be able to dispose the imaging area in line with the needle path 44 axis, which is required to obtain the top-view image, as shown in FIG. 1B. The restricted region 41 relates to the areas that the imaging device 20 is unable to obtain a top-view image, side-view image, or other image because of the structural limitations.

The restricted region 41 may be distinguished from the non-restricted region 42 on the display 33. For example, the processor 31 may generate a marking in the restricted region 41 on the display 33. The marking may be shading, dots, coloring, or other distinguishable marking. The non-restricted region 42 does not have the same marking as the restricted region 41. For example, a user may view the display 33 and distinguish where the restricted region 41 is located and where the non-restricted region 42 is located. Alternatively, the restricted region is not marked and the unrestricted region is marked.

The processor 31 may mark a selected skin entry point 43. The skin entry point 43 may be selected by a physician or user using an input device 34. The processor 31 may mark the user's selected skin entry point 43 using a marking, such as a dot, cross, or other marking, on the display. For example, the marking may be superimposed on the image being displayed on the display 33. As discussed above for the target point marking, the processor 31 may locate and mark the corresponding skin entry points 43 on different images. For example, if a skin entry point 43 was selected on image A of FIG. 5D, the processor 31 may locate the corresponding locations for images B, C, and D and mark the skin entry point 43 locations with the same or different marks.

The processor 31 may prohibit the selection of a skin entry point 43 in the restricted region 41. The restricted region 41 may be displayed on a display 33. The processor 31 may prevent a user from selecting a skin entry point 43 in the restricted region 41. For example, the processor 31 may generate a message conveying that the selected skin entry point 43, which was selected in the restricted region 41, is in the restricted region 41 and that the imaging device 20 is structurally limited from obtaining the necessary images. Alternatively, the processor 31 may only allow a skin entry point 43 to be selected from a region other than the restricted region 41. For example, the user is prevented from selecting a skin entry point 43 in the restricted region 41.

The processor 31 may display as form the needle path 44. The needle path 44 is the path from the skin entry point 43 to the target point (TP). For example, as shown in image A of FIG. 5D, the needle path is a straight line path directly from the selected skin entry point 43 to the selected target point 44. The processor 31 may communicate the needle path 44 to the display 33 or memory 32. The processor 31 may superimpose a needle path 44 marking on an image displayed on the display 33. The marking may be a dashed line, solid line, colored line, or any other marking that illustrates a path from the skin entry point 44 to the target point (TP).

When the needle path is being planned, the imaging system 10 operates to ensure that both the skin entry point 43 and the target point (TP) are located outside the restricted region 41. The path 44 is also verified to be outside the restricted region 41. Accordingly, the physician is ensured that the imaging device 20 will be able to monitor the needle 45 relative to the needle path 44 during the needle 45 progression given the desired views.

Figure 6:
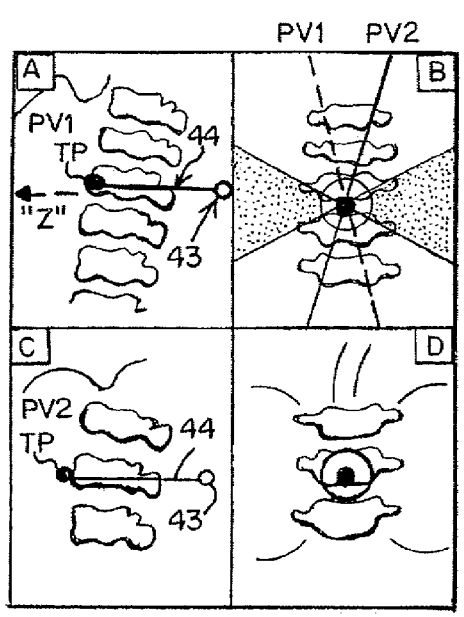
FIG. 6 illustrates one embodiment of a display with fluoroscopic images of a region to be examined displayed thereon.

The processor 31 may define one or more progression views. The progression views may be used during the needle 45 progression. For example, the progression views illustrate the progression of the needle 45 in the patient during the procedure. The progression views PV1, PV2 may be used to ensure that the needle 45 is progressing along the planned needle path 43. The progression views PV1, PV2 may be orthogonal to each other and to the needle path 44. The progression views PV1, PV2 may be selected by the processor 31 based on the structural limitations of the imaging device 20 and/or user input. For example, a fluoroscopic device may be used during a procedure to monitor the progress of the needle 45. The fluoroscopic device may generate, as shown in FIG. 6, a number of fluoroscopic images. The restricted region 41, as shown in image B of FIG. 6, may be displayed on the fluoroscopic image. The progression views PV1, PV2 may be selected from a region 42 outside the restricted region 41. The progression views PV1 and PV2 may be displayed in different images (image A and image C). For example, if a user selects a different progression view PV1, image A will be changed in accordance with the newly selected progression view PV1 with any appropriate restricted region 41.

The memory 32 is a computer readable storage media. The computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 32 may be a single device or a combination of devices. The memory 32 may be adjacent to, part of, networked with and/or remote from the processor 31.

The memory 32 may be a computer readable storage media having stored therein data representing instructions executable by the programmed processor 31 for planning a needle path. The memory 32 stores instructions for the processor 31. The processor 31 is programmed with and executes the instructions. The functions, acts, methods or tasks illustrated in the figures or described herein are performed by the programmed processor 31 executing the instructions stored in the memory 32. The functions, acts, methods or tasks are independent of the particular type of instructions set, storage media, processor or processing strategy and may be performed by software, hardware, integrated circuits, firmware, micro-code and the like, operating alone or in combination. The instructions are for implementing the processes, techniques, methods, or acts described herein.

Figure 7:
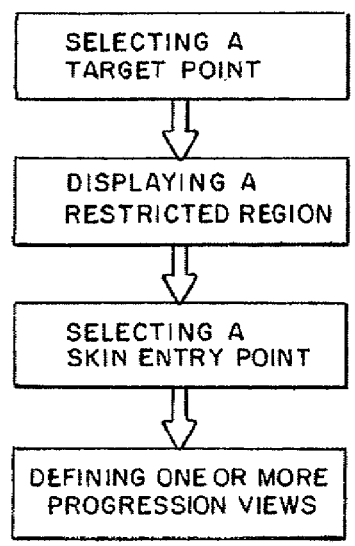
FIG. 7 illustrates one embodiment of a method for planning a needle path.

In one embodiment, a computer readable storage media stores data representing instructions executable by a programmed processor for planning a needle path. For example, as shown in FIG. 7, the storage media may include instructions for selecting a target point or receiving a selected target point; determining a restricted region; and selecting a skin entry point or receiving a skin entry point. The storage media may include instructions for computer-assisted selection of the target point; computer-assisted determination of the restricted region; and computer-assisted selection of the skin entry point. The storage media may include instruction for having a computer or processor 31 determining the restricted region. The restricted region being defined by a structural limitation of the imaging device 20 and a selected target point.

The memory 32 may store structural limitation data for the imaging device 20. As discussed above, the structural limitation data may be defined by any object, movement, or other limitation that restricts the movement of the imaging device 20. For example, the structural limitation data may be defined by the size or position of the patient, the limited number of movements of the imaging device 20, the size or position of the imaging device 20, or any combination thereof. The structural limitation data may be a collection of one or more previously acquired structural limitations. For example, the structural limitations may be determined as part of the installation of imaging device 20, determined on a patient-by-patient basis, or determined by a disk or compact disc for the imaging system. The previously acquired structural limitations may be stored in the memory 32.

The display 33 is a CRT, monitor, flat panel, a general display, LCD, projector, printer or other now known or later developed display device for outputting determined information. For example, the processor 31 causes the display 33 at a local or remote location to output data indicating an image with marked locations of interest; images of the patient, needle, needle path, target point, restricted region or other relevant images; possible C-arm positions; shading; analysis results; medical information from medical records; or other medical decision assistance associated with the current possible c-arm positions or other accessible medical information.

The display 33 may display one or more images. For example, as shown in FIG. 5A, the display 33 may display 2D images, such as a sagittal image (image A), a coronal image (image B), and an axial image (image C). The display 33 may display 3D representations (image D). The sagittal image is an image taken from the side of the patient. The coronal image is an image taken from the front of the patient. The axial images is an image of a slice orthogonal to the long axis of the patient, such as if the patient was cut in half. The sagittal image is a slice image parallel to the long axis of the patient with a viewpoint from left or right of the patient. The coronal image is a slice image parallel to the long axis of the patient with a viewpoint from the front or the back of the patient.

The 3D representation is an image from a volume rendering of the region 60 to be examined. In another example, the display is operable to display images from different angles. The imaging device 30 may have recorded image data from a plurality of different directions. A user may be able to examine all or some of the images generated from the image data by scrolling through, selecting, or analyzing the images as they are displayed on the display 22. Alternatively, additional monitors may be used to display the one or more images.

The display 33 may display a selected target point (TP). The selected target point (TP) may be illustrated as a dot, cross, circle, square, blinking-marker, dash, or other marker indicating a selected location. For example, as shown in FIG. 5B, a target point (TP) may be selected in the 3D representation (image D). The target point (TP) may be marked with a dot. The processor 31 may analyze the location of the selected (TP) in the 3D representation and determine where the target point (TP) is located in the other displayed images (images A, B and C) with or without user assistance. A mark, indicating the location of the selected target point (TP), may be displayed in the other displayed images on the display 33.

The display 33 may display a marker that distinguishes a restricted region 41 of the image from a non-restricted region 42 of the image. As discussed above, the restricted region 41, indicated by shading in FIG. 5, indicates the angles or directions from which the C-arm is spatially limited from obtaining images. The non-restricted region 42 is not shaded in FIG. 5. For example, image A of FIG. 5C is an example of a display with the distinguishing markings of the restricted region 41. In another example, the non-restricted region 42 illustrates an area that a C-arm CT device may be positioned in-line with a needle path 44 axis. In another example, the non-restricted region 42 is the area where the skin entry point may be positioned. A skin entry point located in the non-restricted region 42 will define a needle path that can be examined with the imaging device 30.

Figure 5D:
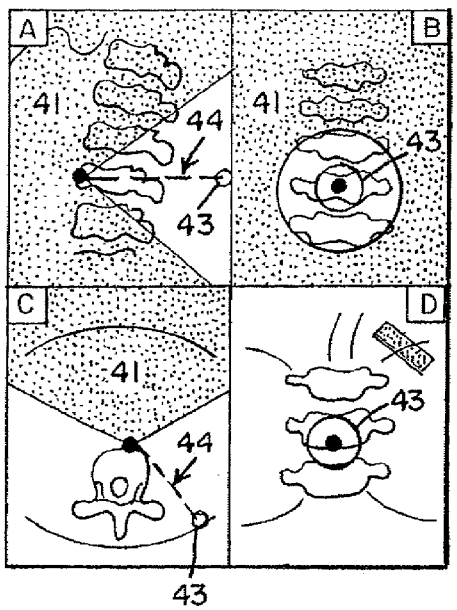

The display 33 may display a selected skin entry point 43. The skin entry point may be illustrated as a dot, cross, circle, square, blinking-marker, dash, or other marker indicating a selected location. For example, as shown in FIG. 5D, a skin entry point 43 may be selected in the 3D representation (image D). In FIG. 5, the skin entry point 43 is marked with a circle. The processor 31 may analyze the location of the skin entry point 43 in the 3D representation and determine where the skin entry point 43 is located in the other displayed images (images A, B and C) with or without user assistance. The display 33 may illustrate the location of the selected target point (TP) in the other displayed images with a marking.

The display 33 may display a planned needle path 44. The planned needle path 44 may be the path from the skin entry point 43 to the target point (TP). The planned needle path 44 may be marked in the images using a dashed line, colored line, solid line, or other representation of a needle path. The needle path 44 may be superimposed on the images. The display 33 may display the needle path 44 on each of the displayed images (images A, B, C, and D). In another embodiment, the processor 31 marks the needle path 44 on images stored in memory 32 for future displays.

The display 33 may display one or more progression images. The progression images may include an in-line image, a side-view image, or a combination thereof. The progression views may be selected progression views or proposed progression views. For example, the progression views may be proposed by the processor 31 and rendered from a 3D dataset. The progression views may be used to visualize the needle progression. For actual progression views, any suitable imaging device 20 may be used to generate a progression image by positioning the imaging device 20 in line with the selected progression view. For example, a fluoroscopy device may be used to generate the one or more progression views.

As shown in FIG. 6, the display 33 may display fluoroscopic images. For example, the one or more progression images (e.g., images A, C, and D) may be fluoroscopic images. In one embodiment, as shown in FIG. 6, flouroscopic image D is an in-line (top-view) image of the needle 45 and needle path 42. The in-line image may be used to determine if the needle 45 is deviating from the needle path 42 in a direction that is orthogonal (perpendicular) to the direction of the needle progression. For example, the in-line image may be used to determine if the needle is deviating from the needle path 42 in the "x" or "y" direction, as shown in FIG. 1A. In another embodiment, as shown in FIG. 6, fluoroscopic image A is a side-view image of the needle 45 and needle path 42. The side-view image may be used to determine the depth of the needle 45 with respect to the skin entry point 43. For example, the side-view image may be used to determine whether the needle 45 has reached the target point (TP) in the "z" direction, as shown in FIG. 1A.

An input device 34 may be a keyboard, computer-mouse, touch screen, voice recognition system, optical recognition system, or any other system for inputting instructions, commands, data, or requests to the imaging system 10. The input device 34 may be controlled by a physician, nurse, or other user of the image processing system. The input device 34 may input information to the image processing system 30. For example, the input device 34 may be operated to select a target point (TP), select a skin entry point 43, scroll through images, select one or more progression views, select patient information from the memory 33, change a previous selection, zoom-in or zoom-out on an image, provide information to the processing system 30, define the positions of the image device 20, defines the images needed to monitor the needle 45, change views of the image, or input any other related or non-related information or command.

FIG. 7 shows a method for planning a needle path. The method is implemented using the system 10 of FIG. 3 or a different system. Additional, different, or fewer acts than shown in FIG. 3 may be provided. For example, in one embodiment, the method may not include act 740. The acts are performed in the order shown or a different order. For example, act 720 may be performed before act 730. The acts may be performed automatically, manually, or combinations thereof.

In act 710, a target point (TP) is defined. Defining the target point (TP) may include obtaining image data, generating one or more images, displaying the one or more images, analyzing the generated images, and determining the location of the end point of the needle path 44. Additional, different, or fewer acts may be provided. For example, act 710 may include inputting user data using an input device 34. In another example, obtaining image data and generating images may be retrieving one or more images from a memory 32 or scanning with a medical image. In another example, the act of displaying the one or more images may be eliminated.

The imaging device 20 may be used to obtain image data. A user, such as an imaging device 20 operator, may manually position and operate the imaging device 20 to obtain the desired image data. Alternatively, the image processing system 30 may position and operate the imaging device 20. The imaging device 20 may receive communications from the image processing system 30. The communications may define positions and angulations of the imaging device 20. The imaging device 20 is positioned into the communicated positions and angulations and obtains images from the positions and angulations. For example, the imaging device 20 may determine a set of imaging positions and angulations based on data supplied to or stored in the image processing system 30. The positions and angulations may be defined by patient data stored in the memory 32 or input using the input device 34. As shown in FIG. 4, the patient data may include patient specific information, such as a patient's weight, patient's height, region 60 to be examined, or other information related to the patient. In another example, the set of imaging positions may be defined by structural limitation data of the imaging device 20. The structural limitation data may include patient support size, patient support height, possible angulations of the imaging device 20, patient data, or other limitations limiting the imaging device 20. The structural limitation data may be stored in the memory 32. In another example, the positions and angulations may be defined by patient data, structural limitation data, and/or other data.

The imaging processing system 30 may generate one or more images using the image data. For example, one or more images (images A, B, C, or D) of a region 60 to be examined may be generated from image data. The one or more images represent the region 60 to be examined. The region 60 to be examined includes the skin surface where the skin entry point 43 is likely to be located.

The one or more images may be displayed on a display 33. For example, as shown in FIG. 5A, a sagittal image is shown in image A, a coronal image is shown in image B, and an axial image is shown in image C. A 3D representation may be generated and displayed in image D. The one or more images may be stored in the memory 32.

The one or more images may be analyzed. In one embodiment, the one or more images may be analyzed by a user, such as a physician, nurse or assistant, using the display 33. The user may use computer assistance to analyze the one or more images. For example, the user may scroll through a plurality of images to find the ones that defines the region 60 to be examined. The plurality of images may include images with different angulations, clarity, sizes, or other image characteristics. In another embodiment, a computer analyzes the one or more images.

The analysis of the image may include defining a location of an end point of the needle path, which normally is the target point (TP). In one embodiment, the target point (TP) is defined by a user. In another embodiment, the target point (TP) is defined by the image processing system 30. The image processing system 30 may define the target point (TP) by analyzing: input data from a user, data stored in the memory 32, a medical ontology, previous examinations, patient data, image analyzing software, or other relevant data, software, or equipment. Once the location of the target point (TP) is defined, the image processing system 30 may mark the target point (TP).

In act 720, the image processing system 30 defines a restricted region 41. Defining a restricted region 41 may include determining the location of the target point (TP) and analyzing the structural limitations of the imaging device 20. Additional, different, or fewer acts may be provided. For example, act 720 may include retrieving a set of structural limitations of the imaging device 20 from the memory 32. In another example, act 720 may include displaying a marking that distinguishes the restricted region 41 from the display 33.

In one embodiment, the restricted region 41 is defined by the location of the target point (TP), the structural limitations of the imaging device 20, and the types of images needed to monitor the progress of the needle during the procedure. The processor 31 may define the restricted region 41. For example, the processor 31 may determine that an in-plane image of the needle path 44 is needed during the procedure. This may be defined by data stored in the memory 32, input by the input device 34, or other analytical process. The processor 31 may then determine the regions 41 that are unable to be examined because of the structural limitations of the imaging device 20.

The restricted region 41 may be displayed on the display 33. For example, as shown in FIG. 5C, a marking that illustrates the restricted region 41 may be superimposed on the one or more images (images A, B, C, and D). The restricted region 41 may be illustrated on the display 33 with shading, dots, color, non-shading, or any other marker that distinguishes the restricted region 41 from the non-restricted region 42. Similarly, the non-restricted region 42 may be illustrated with any marker that distinguishes it from the restricted region 41. The distinguishing marker makes it visible on the display which area, the non-restricted region 42, may be used to plan a needle path 44.

In act 730, a needle path 44 is defined. Defining the needle path 44 may include selecting a skin entry point 43 in a region 42 other than the restricted region 41. Additional, different, or fewer acts may be provided.

A skin entry point 43 may be selected from a region 42 other than the restricted region 41. In one embodiment, a user views the restricted region 41 and the non-restricted region 42 and selects the skin entry point 43 using the input device 34. For example, the user may select the location of the skin entry point 43 using a mouse and cursor. A skin entry point 43, which is viewable from the necessary positions and angulations with the imaging device 20, is defined when the cursor is located in the non-restricted region 42. The user may select the skin entry point 43 based on the surrounding body parts. In another embodiment, the image processing system 30 selects the skin entry point 43. For example, the image processing system 30 may identify the skin entry point 43 that will minimize the number of other organs that the needle 45 must proceed through before reaching the target point (TP).

The needle path 44 is defined by the location of the target point (TP) and the skin entry point 43. The beginning of the needle path 44 is the skin entry point 43 and the end of the needle path 44 is the target point (TP). Generally, the needle path 44 is a straight line path; however, it may be curved.

In act 740, one or more progression views are defined. The progression views may be defined by the types of images needed to monitor the progress of the needle 45 during the medical procedure, the structural limitations of the imaging device 20, and the location of the target point (TP). Defining one or more progression views may include displaying a restricted region 41 on a display 33 and selecting the progression view PV1 or PV2 from the non-restricted region 42. The progression views may be proposed by the processor 31 or selected by a user. Since the imaging device 20 used for monitoring the progression of the needle 45 during the medical procedure is the same or substantially the same imaging device used to obtain the image data during the planning stage, the same or substantially the same restricted region 41 may be used during the medical procedure to monitor the progress of the needle 45. Additional, different, or fewer acts may be provided.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A method for planning a needle path, the method comprising:
    displaying an image on a display, the image being of a region of a patient to be examined;
    superimposing a representation of a restricted region on the displayed image, the restricted region being defined, using a processor, by spatial limitations of an imaging device, a type of progression image to be generated, and a location of a selected target point, the displayed image being different than the progression image, wherein the spatial limitations of the imaging device prevent the imaging device from moving into one or more positions relative to the patient for generating the progression image to monitor progress along the needle path; and
    selecting the needle path outside the restricted region,
    wherein selecting the needle path includes selecting a skin entry point outside the restricted region, the processor preventing selection of the skin entry point within the restricted region.

2. The method for planning a needle path as defined in claim 1, wherein the imaging device includes a C-arm computed tomography device.

3. The method for planning a needle path as defined in claim 2, wherein spatial limitations of the C-arm computed tomography device include C-arm angulations.

4. The method for planning a needle path as defined in claim 1, comprising: inputting user data,
    wherein the selected target point is defined by the user data.

5. The method for planning a needle path as defined in claim 4, comprising: generating the user data by viewing one or more images of an examination area.

6. An imaging system for planning a needle path, the imaging system comprising:
    a display;
    a processor electrically connected to the display; and
    an imaging device electrically connected to the display and the processor,
    wherein the processor is configured to determine a restricted region defined by spatial limitations of the imaging device, a type of progression image to be generated, and a location of a target point of the needle path, the one or more spatial limitations of the imaging device preventing the imaging device from moving into one or more positions relative to a patient for generating the progression image to monitor progress along the needle path, wherein the display is operable to display an image and a representation of the restricted region superimposed on the image, the image being of a region of a patient to be examined, the displayed image being different than the progression image, and wherein the processor is configured to prevent selection of a skin entry point of the needle path within the restricted region.

7. The imaging system for planning a needle path as defined by claim 6, wherein the processor is operable to superimpose the representation of the restricted region on the image.

8. The imaging system for planning a needle path as defined by claim 6, wherein the imaging device includes a C-arm computed tomography device.

9. The imaging system for planning a needle path as defined by claim 6, wherein the imaging device includes a C-arm fluoroscopic device.

10. The imaging system for planning a needle path as defined by claim 6, comprising: an input device electrically connected to the processor.

11. The imaging system for planning a needle path as defined by claim 6, comprising: a memory electrically connected to the processor.

12. A non-transitory computer readable storage media having stored therein data representing instructions executable for planning a needle path, the instructions comprising:

displaying an image on a display, the image being of a region of a patient to be examined;

superimposing a representation of a restricted region on the displayed image, the restricted region being defined by spatial limitations of an imaging system, a type of progression image to be generated, and a location of a target point, the displayed image being different than the progression image, wherein the spatial limitations of the imaging system prevent the imaging system from moving into one or more positions relative to the patient for generating the progression image to monitor progress along the needle path; and preventing selection of a skin entry point of the needle path within the restricted region.

13. The computer readable storage media as defined in claim 12, the instructions comprising: reading a set of spatial limitations stored in the non-transitory computer readable storage media.

14. The computer readable storage media as defined in claim 12, the instructions comprising: selecting the target point location.

15. The computer readable storage media as defined in claim 14, the instructions comprising: selecting a skin entry point location at a location disposed outside of the restricted region.

16. The computer readable storage media as defined in claim 15, the instructions comprising: defining the needle path as a path between the target point and the skin entry point.

17. A method for monitoring a needle progression during a medical procedure, the method comprising:

displaying an image on a display, the image being of a region of a patient to be examined and being an image type, the image type being in an image plane at an orientation relative to the patient;

superimposing a representation of a restricted region on the displayed image of the region to be examined, the restricted region being defined, using a processor, by spatial limitations of an imaging system, a type of progression image to be generated, and a location of a needle path, the displayed image being different than the progression image;

selecting the progression image that is disposed outside the restricted region; and monitoring the needle progression using the progression image, wherein the spatial limitations of the imaging system prevent the imaging system from obtaining the progression image for at least part of the restricted region, the progression image being in a progression image plane, the progression image plane being at an orientation different than the image plane and relative to the needle path.

18. The method as defined by claim 17, wherein the progression image includes a top-view image that is in-line with the needle path, a side-view image that illustrates a depth of the needle, or the top-view image and the side-view image.

19. The method as defined by claim 18, wherein the progression image is a fluoroscopic image.

20. The method as defined by claim 18, wherein monitoring the needle includes switching from monitoring the top-view image to monitoring the side-view image.

21. The method as defined by claim 18, wherein the restricted region is an area that an imaging device is physically unable to obtain the selected progression image.

* * * * *